United States Patent [19] [11] 4,419,986
Leibo [45] Dec. 13, 1983

[54] EMBRYO TRANSFER APPARATUS

[75] Inventor: Stanley P. Leibo, San Antonio, Tex.
[73] Assignee: Rio Vista International, Inc., San Antonio, Tex.

[21] Appl. No.: 438,596
[22] Filed: Nov. 2, 1982

Related U.S. Application Data

[62] Division of Ser. No. 251,969, Apr. 7, 1981, Pat. No. 4,380,997.

[51] Int. Cl.³ .......... A61B 19/00
[52] U.S. Cl. .......... 128/1 R
[58] Field of Search .......... 604/19, 55; 128/1 R

[56] References Cited

U.S. PATENT DOCUMENTS

| | | | |
|---|---|---|---|
| 3,490,437 | 1/1970 | Bakondy et al. | 128/1 R |
| 3,811,443 | 5/1974 | Dickinson et al. | 604/55 |
| 3,854,470 | 12/1974 | Augspurger | 128/1 R |
| 3,866,598 | 2/1975 | Augspurger | 128/1 R |
| 3,906,929 | 9/1975 | Augspurger | 128/1 |
| 3,940,943 | 3/1976 | Sikes et al. | 128/1 R |
| 3,943,993 | 3/1976 | Smith | 128/1 R |
| 4,007,367 | 2/1977 | Rusteberg et al. | 128/1 R |

FOREIGN PATENT DOCUMENTS

| | | | |
|---|---|---|---|
| 2459321 | 6/1976 | Fed. Rep. of Germany | 604/55 |

OTHER PUBLICATIONS

George E. Seidel, Jr., "Superovulation and Embryo Transfer in Cattle", *Science* magazine, Jan. 23, 1981, vol. 211, No. 4479.

Dr. R. Peter Elsden, "Bovine Embryo Transfer," *American Breeds Journal,* pp. 18-26, Nov. 1980.

D. G. Whittingham, et al., "Survival of Mouse Embryos Frozen to −196° and −269°", *Science* magazine, Oct. 27, 1972, vol. 178, pp. 411-414.

Wilmut, et al., "Experiments on the Low-Temperature Preservation of Cow Embryos," *The Veterinary Record,* Jun. 30, 1973, pp. 686-690.

Y. Tsunoda, et al., "Survival of Rabbit Eggs Preserved in Plastic Straws and Liquid Nitrogen," J. Reprod. Fert. (1977) 49, 173-174.

Trounson, et al., "Non-surgical Transfer of Deep--Frozen Bovine Embryos", *Theriogenology,* Jul. 1978, vol. 10, No. 1, pp. 111-115.

Leibo, et al., "Methods for the Preservation of Mammalian Embryos by Freezing," Methods in Mammalian Reproduction, 1978, pp. 179-201.

*Primary Examiner*—C. Fred Rosenbaum
*Assistant Examiner*—T. J. Wallen
*Attorney, Agent, or Firm*—Richards, Harris & Medlock

[57] ABSTRACT

A method for storing, thawing and transferring frozen embryos to recipient animals is disclosed which provides the advantage of a one step dilution, to eliminate damage from the cryoprotective solution after thawing, and immediate transfer to the recipient animal. Also disclosed is an apparatus for freezing, storing, thawing and transferring frozen embryos to recipients which comprises a container having first and second chambers wherein a volume of cryoprotective solution containing the embryo can be stored in the first chamber and an effective volumetric amount of a diluent solution can be stored in the second chamber the chambers being divided by removable separation means so as to provide for a dilution process within a single field container.

12 Claims, 2 Drawing Figures

EMBRYO TRANSFER APPARATUS

This is a division of application Ser. No. 251,969 filed Apr. 7, 1981, now U.S. Pat. No. 4,380,997.

TECHNICAL FIELD

The present invention relates to embryo storage and transfer techniques wherein an embryo is recovered from a donor animal, frozen for storage purposes and then thawed and transferred to a recipient animal in which the embryo can develop and be delivered by the recipient. Thus, this invention relates both to cryobiology and embryology. One aspect of the invention relates to a method for freezing and storing living embryos for the purpose of later thawing and transferring same to a recipient animal. Another aspect of the invention relates to an improved method for thawing and transferring embryos to a recipient animal. In a still further aspect, this invention relates to an apparatus for freezing an embryo, storing same, and then thawing and transferring the embryo to a recipient animal.

BACKGROUND ART

In recent years the ability to transfer embryos from donor animals to recipient animals, linked with the ability to cause genetically superior females to superovulate has resulted in commercial feasibility for the use of embryo transfer as a method of improving both the quality and quantity of domestic animals, and in particular, cattle. The basic steps of embryo transfer include, inducing superovulation (for example, through use of gonadotropin treatment), fertilization (either naturally or through artificial insemination), recovery of embryos from the donor, and either surgical or nonsurgical transfer to a recipient which is at the same stage of the estrous cycle as was the donor at the time of recovery. Until recent years one major obstacle to the widespread use of embryo transfer procedures was the biological requirement that the recipients be at the same stage of the estrous cycle as the donor, on in other words, in the terminology of the discipline, be synchronized. If a proper number of synchronized recipients were not available at the time of embryo recovery from the donor, either wastage would occur or storage of the embryos was necessary until a prospective recipient came into synchronization. Until recently such storage was usually limited to a short time (a matter of hours) since embryo survival in vitro beyond such length of time was impractically low.

Recently, however, the science of cryobiology has provided technology whereby storage of embryos recovered from donors can be almost indefinite through the use of freezing techniques. Thus, through the marriage of the sciences of embryology and cryobiology it is now possible to recover multiple embryos of genetically desirable makeup through superovulation and embryo recovery techniques, store the embryos indefinitely by freezing same, and thaw and transfer the embryos to healthy and desirable recipients at the proper stage of their estrous cycle at the convenience of the transferor.

Methods for superovulating prospective donors, recovering embryos either surgically or nonsurgically, and transferring the embryos to a donor are fairly well known. However, the use of cryobiological techniques to freeze an embryo for storage purposes and then thaw same in a manner which keeps the embryo viable, in the sense that a successful transfer and resulting pregnancy can occur, is a more recent development and to date has required fairly skilled technicians and special equipment.

Thus, presently the standard method for storing embryos by freezing begins by exposing the embryos to a liquid cryoprotective agent, usually in a stepwise manner, wherein the concentration of the cryoprotective agent is increased in each of three steps. Many presently employed cryoprotective agents are permeating compounds i.e., they actually enter the cells of the embryo. Thus, stepwise exposure to the agent allows the embryo to be permeated in a manner which avoids damage to the cell. Once a sufficient amount of the cryoprotective agent has permeated the embryo, a volume of the liquid cryoprotective agent containing the embryo is cooled, typically in a container such as a glass ampule, in a stepwise manner from room temperature to a temperature slightly below the freezing point of the particular cryoprotective agent. At that temperature the sample is "seeded" to induce ice formation. Then a further controlled stepwise lowering of temperature occurs until finally the ampule containing the frozen cryoprotective agent and embryo can be transferred for storage into liquid nitrogen at −196° C.

The most commonly employed techniques used by those skilled in the art for thawing the embryos contained in the ampules include raising the temperature at a moderately rapid rate by transferring them directly from liquid nitrogen into a 20° C. or 37° C. water bath. However, once the embryos are recovered from the ampules, along with the volume of liquid cryoprotective agent, a stepwise dilution of the cryoprotective agent is conventionally employed in order to avoid cellular damage. The cryoprotective agent must be removed from the embryo's environment if the embryo is to remain viable after transfer. Because a rapid change in osmotic pressure across the cell membrane of the embryo can cause harmful cellular damage, the removal of the cryoprotective agent (which as noted above, in most cases has penetrated the embryo) must be done slowly and conventionally includes a six step process wherein the embryo is placed in solutions of cryoprotective agent having consecutively lesser concentrations so that the dilution occurs slowly enough to avoid cellular damage.

The above-described freezing and thawing techniques, which must be employed if the convenience of long-term storage of embryos is to be available, require moderately skilled technical assistance as well as a microscope and other laboratory equipment. Furthermore there is risk of embryo damage and/or loss due to the handling and transferring of the embryo during the thawing and transferring process. Therefore, a method for freezing and thawing embryos between recovery and transfer which requires less handling of the embryo and simpler procedures, which could be carried out in the absence of laboratory facilities, would be especially desirable. Further, apparatus which would allow substantial elimination of handling of the embryo between the time of its recovery and transfer, and which could be used to directly transfer the embryo would also be desirable.

DISCLOSURE OF INVENTION

The improved thawing and transfer methods of the present invention simplify the steps, procedures and equipment necessary to successfully freeze an embryo for storage, thaw the embryo, and transfer same to a recipient. As used herein the term "embryo" in defined to mean both fertilized ova and unfertilized ova even though technically an ovum only becomes an embryo after being fertilized.

More particularly, the present invention provides a method for thawing frozen embryos which can be performed in the field at the location of the recipient animal. This is of great advantage since present techniques generally require that the recipient either be transported to, or kept at, a facility where the multistep dilution process necessary to remove the cryoprotective agent can be performed. In a preferred embodiment of the present invention, the transfer of the embryo from frozen storage to the recipient animal can be performed in the field much in the same manner as is employed in present artificial insemination techniques using frozen semen. This preferred embodiment of the invention includes the use of a sealed container in which the embryo is frozen in a volume of cryoprotective agent and in which is also present a diluent such that upon removing the container from storage in liquid nitrogen to thaw same, the diluent and volume of cryoprotective agent containing the embryo can be admixed and the dilution occur within the sealed container. Transfer of the embryo can then be performed by directly depositing the contents of the sealed container in the uterus of the animal, either surgically or nonsurgically.

In a most preferred embodiment of the subject invention, the sealed container is in the form of an artificial insemination straw which can be used in conjunction with an artificial insemination gun to perform nonsurgical transfer of the embryo to the recipient, the embryo never having left the sealed container in which it was frozen and stored.

The unique thaw and transfer technique of the present invention utilizes the physiology of the embryo itself to provide a method whereby a one step dilution of the cryoprotective agent occurs. Thus, in general, the thaw and transfer techniques of the subject invention comprise the steps of allowing a volume of frozen cryoprotective agent containing an embryo in frozen storage to reach ambient temperatures in an uncontrolled manner, diluting the cryoprotective agent by combining therewith an effective volumetric amount of a solution of a nontoxic, nonpermeating diluent, the concentration of the diluent in the diluting solution being such that the resulting mixture of cryoprotective agent and diluent solution is isosmolal, and finally transferring the dilution mixture directly to the body of the recipient animal where the dilution mixture itself is washed away (or diluted) by the body fluids of the animal.

The above dilution and transfer method allows the physical manipulation of the embryo during thawing and transfer to be greatly reduced. Thus, by using a single sealed container having a first chamber with the volume of cryoprotective agent and embryo contained therein and a second chamber containing the diluent solution, the container being constructed so as to allow the separation means separating the two chambers to be removed, the thaw and transfer process is reduced to the steps of (a) thawing of the container from storage temperature to ambient temperature, (b) removing the chamber separation means to allow the volume of cryoprotective agent to contact the diluent solution and, after allowing enough time for dilution of the cryoprotective agent to occur, (c) opening the sealed container and transferring the entire contents thereof directly into the recipient animal either surgically or nonsurgically.

DETAILED DESCRIPTION

Figure 1:
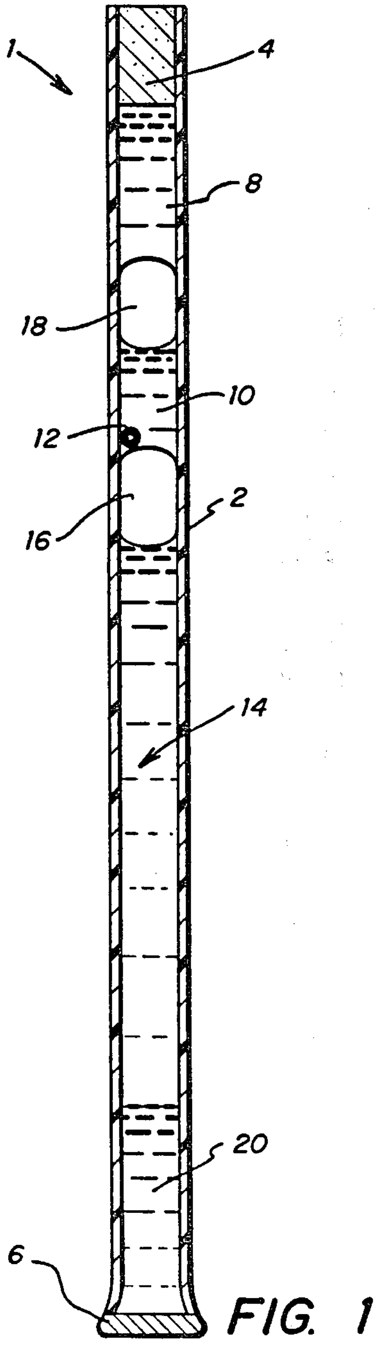
FIG. 1 is a cross-sectional schematic view of an elongated tubular container having two portions of cryoprotective agent in the upper section thereof, an embryo in the second portion of cryroprotective agent, and a volumetric amount of diluent solution in the lower section thereof with air bubbles separating the liquid portions.

As noted above, current embryo transfer technology includes obtaining embryos either singly, or in multiples through induced superovulation procedures from a donor, the recovery techniques being performed either surgically through incision into the uterus of the female donor or nonsurgically by flushing of the uterus. Once collected, the embryos are normally inspected and classified and othewise preliminarily processed before they are prepared for freezing.

While the precise freezing techniques employed will depend upon the species of the embryo, the freezing process conventionally includes at least the following procedures. The embryo is transferred from a culture medium such as phosphate-buffered saline (hereinafter sometimes referred to as PBS) to a volume of an appropriate concentration of a cryoprotective agent. The function of the cryoprotective agent is to protect the embryo from damage caused by freezing. For example, it is known that one source of damage is intracellular ice formation. While it is contemplated that the cryoprotective agents can be both of a permeating and nonpermeating type, the most conventional cryoprotective agents are "permeating" in the sense that they actually enter into the embyro itself. Common permeating cryoprotective agents include dimethyl sulfoxide (DMSO) and glycerol, for example, contained in concentrations of from about 0.5 M to about 2.0 M in phosphate-buffered saline. Another example of such cryoprotective agents are the low molecular weight glycols, e.g. ethylene glycol and diethylene glycol. Common nonpermeating cryoprotective agents include polyvinyl pyrrolidone (PVP) ad hydroxyethyl starch (HES). Those skilled in the art will recognize that phosphate-buffered saline is a commonly used aqueous solution of phosphate-buffered salts. As used herein the term "PBS"]is defined to mean an aqueous solution of phosphate-buffered salts of substantially isotonic concentration and neutral pH. Thus, depending upon the developmental stage and species of embryo being frozen, the correct concentration and type of cryoprotective agent is supplied and then the volume of cryoprotective agent (normally in the form of a PBS solution thereof) is frozen, using a variety of freezing techniques employing controlled, time dependent, temperature reductions.

After the volume of cryoprotective agent containing the embryo has been frozen it can be stored conveniently in liquid nitrogen at −196° C. over long periods of time. Mamalian embryos frozen and stored in this manner have been known to survive and develop into normal animals after having been stored up to five years.

The stored frozen embryo contained in the volume of cryoprotective agent must be thawed for transfer to the recipient animal. In some cases the thawing process is time and temperature controlled. In other cases, depending upon the particular embryo and cryoprotective agent employed, thawing can be achieved simply by removing the container in which the volume of cryoprotective agent and embryo have been stored from a liquid nitrogen storage container and allowing the embryo container to reach ambient temperatures in an uncontrolled manner. Once the volume of cryoprotective agent and embryo have thawed, i.e., changed from a frozen solid state to a liquid state, it is necessary to dilute or wash away the cryoprotective agent from the embryo if a viable embryo is to result.

While most conventional dilution procedures employ a multistep process whereby the cryoprotective agent is diluted away by reducing its concentration in a stepwise fashion, it is impossible to achieve a one step dilution by employing an effective volumetric amount of a solution of a nontoxic, nonpermeating diluent, the concentration of the diluent being such that upon admixture with the cryoprotective agent the resulting liquid mixture is substantially isosmolal. As used herein the term "diluent" refers to a nontoxic, nonpermeating (i.e., incapable of substantial permeation into the embryo) substance of sufficient solubility in water to be able to obtain the concentrations necessary to achieve the isosmolal condition described below. The preferred diluent is sucrose. The term "diluent solution" as used herein refers to a solution of the diluent in PBS, the concentration of the diluent being determined as a function of the concentration and type of cryoprotective agent to be employed and the relative volumetric proportion of the volume of cryoprotective agent to the volume of diluent solution. Finally, as referred to herein, the term "dilution mixture" refers to the isosmolal liquid solution which results from a combination of the diluent solution with the volume of cryoprotective agent containing the embryo.

The one step dilution procedure requires that the resulting dilution mixture meets two conditions, if a viable embryo is to result. First, the concentration of the cryoprotective agent and the concentration of the diluent must be such so that they are isosmolal, i.e. that they have approximately the same osmolalities. Such a condition provides essentially a zero osmotic pressure gradient across the membranes of the embryo. At the same time, however, any cryoprotective agent which may have penetrated the embryo leaves the embryo through diffusion due to the much lower concentration of cryoprotective agent in the dilution mixture. Thus, removal of the cryoprotective agent from the interior of the embryo is effected without harmful cellular damage which can occur if osmotic pressure is not controlled. Secondly, the dilution mixture reduces the overall concentration of the cryoprotective agent in the fluid surrounding the embryo. Thus, for example, a ten to one dilution (ten volumes of diluent solution per one volume of cryoprotective agent) results in the dilution mixture having one-tenth the concentration of cryoprotective agent as was present during the freezing and storage process. Those skilled in the art will thus recognize that both the concentrations of the diluent and cryoprotective agent and the relative volumetric proportion of cryoprotective solution to diluent solution can be adjusted to obtain a final dilution mixture having the characteristics necessary for a successful one step dilution.

Once a sufficient amount of time has elapsed to allow the embryo to undergo the one step dilution process described above, it is necessary to wash away or remove (or, in fact, dilute) the dilution mixture from the environment of the embryo. It has now been discovered that, in effect, a one step dilution of the dilution mixture away from the embryo can be effected at slightly elevated temperatures, for example, the body temperature found within the uterus of the recipient animal. Thus, by transferring the dilution mixture directly from its container into the recipient animal either surgically or nonsurgically, the elevated temperature conditions within the animal will be sufficient to allow the embryo to acclimate itself to normal body fluid conditions as compared to the artificial conditions it is subjected to while suspended in the dilution mixture.

Those skilled in the art will recognize that the precise processing parameters, cryoprotective agents, diluents and concentrations and volumetric proportions of each, will be the dependent upon the biological requirements of the particular embryo being transferred. The following procedure exemplifies, without limiting, the transfer method of the present invention.

Bovine embryos, recovered from suitable donors and suitably inspected and classified are introduced into a PBS solution of glycerol in a concentration ranging from about 1.5 M to about 2.0 M, in a single step. After the bovine embryos contact the glycerol solution for a time period ranging from about five to about thirty minutes, in temperatures ranging from about 20° C. to about 37° C., they are cooled in an aliquot of the glycerol solution by cooling in a single step from ambient conditions to just below the freezing point of the cryoprotective solution. The samples are then seeded (a technique well known to those in the science of cryobiology) and then further cooled down to about −35° C. at a rate of about 0.5° C. per minute. The embryos are then held at this temperature for about thirty to sixty minutes and plunged directly into liquid nitrogen for storage at −196° C.

Thawing of the samples can be accomplished rather rapidly at rates, for example, of up to about 100° C. to 400° C. per minute. A convenient thawing process simply comprises removing the frozen sample from the liquid nitrogen and allowing it to reach ambient conditions, a step requiring from about one to about two minutes. Upon reaching ambient temperature, the embryos contained in the volume of glycerol solution are diluted at least sixfold and preferably about tenfold with a sucrose solution that is equal in osmolality with the glycerol solution. The resultant dilution mixture is then held at room temperature for about ten to about thirty minutes and then transferred either surgically or nonsurgically into the recipient animal.

Another embodiment of the present invention is an apparatus which can be used to store the frozen embryo, achieve the above outlined dilution process and transfer the dilution mixure to the recipient without the need to physically manipulate the embryo or separately prepare and admix the necessary liquid constituents. The apparatus of the present invention can be fabricated from a variety of materials and in a variety of shapes so long as it has the characteristics set forth below.

Thus, in general, the apparatus comprises a container having at least two chambers separated by a removable separation means so that the user can cause the interior of the first chamber to communicate with the interior of the second chamber when desired. Contained in the first chamber is a volume of cryoprotective agent (usually in a PBS solution) and the embryo which is to be transferred. In the second chamber of the container is a premeasured and mixed diluent solution, the volumetric amount of said diluent solution in the second chamber being effective to dilute the volume of cryoprotective agent to a sufficiently low and nonharmful concentration in the dilution mixture, and the concentration of the diluent contained in the diluent solution being such that the dilution mixture will be isosmolal. In a preferred embodiment, the container can be completely sealed so as to protect the embryo from leakage during storage.

The above-described apparatus can be easily constructed just prior to the freeze-storage process. Thus, for example, the aliquot of cryoprotective agent containing the embryo can be deposited in the first chamber of the container and the premeasured and mixed diluent solution can be deposited in the second chamber of the container and then the entire container can be subjected to a conventional type freezing process for storing the embryo. When a suitable recipient is selected and has been determined to be in synchronization with the stored embryo, the container can then be removed from storage and allowed to come to ambient conditions and the removable separation means separating the chambers can be removed to allow the one step dilution process described above to take place. Transfer of the dilution mixture containing the embryo directly into the recipient animal can then be accomplished directly by transferring the contents of the container to the animal either surgically or nonsurgically.

One preferred embodiment of the apparatus employs sterile plastic straws of very fine diameter such as are conventionally used in artificial insemination techniques. Such straws are familiar to those skilled in the art and can, for example, be what are known to those in the artificial insemination industry as "French straws" such as those marketed by I.M.V. of L' Aigle, France. Such straws can be purchased in either colored or clear varieties and come in various sizes including, for example, a 0.5 cc capacity straw and a "fine" straw having a capacity of 0.25 cc. Many of these straws include a sealing powder, or plug, which is made of a dry porous material which seals once it becomes moist. Such straws can be used with artificial insemination guns which effectively push the sealing plug through the interior diameter of the straw thereby forcing all the liquid material contained in the straw out its open end.

Now referring to FIG. 1, one particularly preferred embodiment of the apparatus of the present invention will be described. FIG. 1 is a cross section of a tubular container 1 which, though schematically represented could be, for example, the plastic artificial insemination straws described above. Thus, the tubular container wall 2 is sealed at its first end by porous sealing plug material 4 and at its second end by a heat seal 6 causing the end thereof to flange out but be completely sealed. In the upper end of the tubular container 1 is a first portion 8 of a solution of a cryoprotective agent, such as glycerol in a PBS solution, for example. A second volume of cryoprotective agent 10 contains the embryo 12 which is to be transferred. In the lower portion of the tubular container 1 is a premeasured volumetric amount of a diluent solution 14, the concentration of the diluent being such that when the cryoprotective agent contained in first portion 8 and volume 10 are combined therewith the resulting dilution mixture will be isosmolal. The tubular structure 1 is, in essence, separated into three chambers by means of air bubbles 16 and 18. Thus, the particular embodiment of the apparatus of the invention illustrated in FIG. 1 comprises a tubular container 1 separated into three chambers by two removable separation means (air bubbles 16 and 18).

The first portion 8 of the cryoprotective agent merely functions as a sealing aid and allows an additional separation means, in the form of air bubble 18 to be placed within the container to ensure that if the container is turned upside down, the embryo 12 will not come into contact with plug material 4. A second chamber located between air bubbles 16 and 18 contains a volume of cryoprotective agent 10 and the embryo 12 is thus insulated from any deleterious contact from either above or below. The final chamber of the tubular container 1, as described above, contains a premeasured effective volumetric amount of a diluent in a PBS solution at a proper concentration.

In a preferred embodiment, a liquid cushioning substance 20, which can be color coded using a nontoxic dye substance, is provided at the bottom of tubular container 1. The liquid cushioning agent can be any of a number of nontoxic relatively viscous materials such as a saturated solution of sucrose, for example, through which the embryo (when released from the separate chamber as described below) will not pass under either gravitational or moderate centrifugal forces.

One preferred technique for fabrication of the apparatus shown in FIG. 1 is to employ a 0.25 cc French straw (as described above) which conveniently mounts in the aperture of a 1 ml plastic syringe, drawing the first portion 8 of cryoprotective agent up into the staw, allowing the straw to aspirate air bubble 18, drawing the volume 10 of cryoprotective agent, containing embryo 12, up into the straw, again allowing the straw to aspirate air bubble 16, and finally drawing, through use of the syringe, the correct volumetric amount of diluent solution 14 and liquid cushioning substrate 20. The straw can then be heat sealed and the embryo frozen according to conventional cryobiological techniques for storage purposes.

Figure 2:
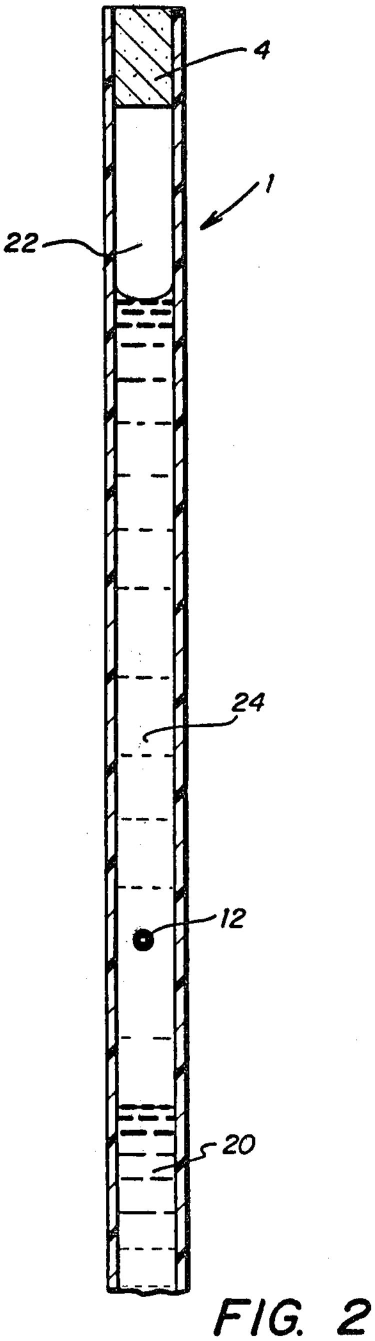
FIG. 2 is a cross section of the elongated tubular container of FIG. 1 after the air bubble separation means have been removed allowing the cryoprotective agent and embryo to contact the diluent solution.

FIG. 2 illustrates tubular container 1 which is ready for transfer of the dilution mixture directly into the recipient animal. Thus, in use, the tubular container (such as the French staws described above) can be removed by the user from the liquid nitrogen storage container, allowed to come to ambient conditions (which in the case of the French straw and moderate temperatures will normally occur over a period of from about one to about two minutes depending on the ambient temperature conditions, storage conditions and the construction of the container). The tubular container 1 is then subjected to centrifugal force. While typical laboratory centrifuges can be employed (e.g., at relative centrifugal forces (RCF) of from about 100 to about $200\times G$), it has been found that when French straws are used as tubular container 1, enough centrifugal force can be generated by simply swinging the arm in an arc, or even by shaking the French straw in much the same manner as one would shake down an ordinary clinical thermometer. This operation removes the bubble separation means by causing the bubbles to rise to the top of tubular container 1 forming one composite bubble 22 and allowing the cryoprotective agent and diluent solution to come into contact and form dilution mixture 24.

After allowing sufficient time for the one step dilution process to proceed at room temperature, for example, from about ten to about thirty minutes, the heat seal 6 at the bottom of tubular container 1 can be snipped off and, in the case of an artificial insemination straw, the tubular container can be placed in an artificial insemination gun and the contents thereof delivered from the tubular container 1 by pressing plug 4 along the interior thereof to deliver the embryo and dilution mixture directly into the recipient animal, either surgically or nonsurgically using conventional transfer techniques. Optionally, the contents of the container can be delivered to a culture medium for observation or other procedures preliminary to the actual transfer. The liquid cushioning substance 20 ensures that when the user cuts off the tip of the tubular container 1 in order to make the transfer he does not lose or harm the embryo, since even during centrifugation it has not penetrated the cushioning substance 20. Thus, by employing a suitable nontoxic dye in the liquid cushioning agent, the user can be instructed that loss of the embryo will be avoided so long as the straw, or tube, is cut in the colored region.

In a most preferred embodiment of the apparatus of the subject invention the cushioning substance is not employed. In all other respects the embryo is loaded into the French straw and frozen as described above. After the straw has been thawed it is centrifuged "upside down", i.e. the centrifugal force is directed from heat seal 6 toward the end of container 1 containing plug material 4. Therefore the diluent solution 14 is forced down into the volume of cryoprotective agent 10 containing embryo 12 and against the first portion 8 of cryoprotective agent. In this case the air bubble 22 (as depicted in FIG. 2) would be present at the "bottom" of the straw just above the heat seal 6. This method assures good mixing of the various components of the system. It should be noted that it is not absolutely necessary to use the plug material 4 and a heat seal could also be used at this end of the container 1. Further, in the most preferred embodiment described above the user can be instructed to snip off the end of the tubular container wherein the air bubble is present to guard against loss or damage of the embryo.

While not strictly necessary it is preferable to ensure good mixing of the cryoprotective agent and diluent by subjecting the contents of the straw to a gentle mixing action, for example, in any of a variety of laboratory rocking devices. One apparatus which has been found to be useful for this purpose is commonly used for conducting tests for the presence in cattle of the bacterium *Brucella abortus*. Such gentle mixing can be imparted for a portion or all of the dilution period, which usually ranges in length from about 15 to about 30 minutes.

When employing a plastic flexible tube as the container portion of the apparatus of the present invention, the fitting of a handle to the top portion thereof aids both the handling of the container (such as placing and removing the embryo container into and out of a frozen storage apparatus) and also provides a means by which an embryo can be labeled with important identification information. One convenient method for providing such a handle, for example, is to employ a 0.5 cc artificial insemination straw slipped over the end of the 0.25 cc straw which is used as tubular container 1 as described above. In this manner, handling will be facilitated and premature thawing, as well as loss of identification information, will be avoided.

EXAMPLE

The following example is provided to facilitate the understanding of one preferred embodiment of the present invention and not for the purpose of limiting same. Those skilled in the art will recognize that various modifications in the procedure outlined below including, for example, variations in the type, concentrations, and volumetric amounts of cryoprotective agent and diluent and the apparatus used in connection with these materials can be used for the purpose of practicing the present invention.

Bovine embryos, at the blastocyst stage of development are recovered from a genetically desirable donor cow, approximately six to eight days after artificial insemination, with the use of a Foley catheter. Through microscopic examination the embryos are isolated and classified. Embryos are then incubated in a 2.0 M glycerol-PBS solution which also contains ten percent by weight fetal calf serum at room temperature for approximately fifteen minutes. A 0.25 cc artificial insemination straw is then inserted in the aperture of a 1 ml disposable plastic syringe and the first small portion of the 2.0 M glycerol solution is drawn up into the straw. Next a small air bubble is aspirated into the end of the straw. The tip of the straw is then inserted into the dish containing the incubated embryos and a second portion of the glycerol solution and a single embryo is drawn up into the straw. A second air bubble is then aspirated into the straw and finally a volumetric amount of a 1.08 M sucrose solution in PBS is drawn into the straw, the relative volume of the sucrose solution to the total amount of glycerol in the straw being a ratio of approximately 10:1. Finally, a liquid cushioning material in the form of about 2 M sucrose solution in PBS which has been dyed to a blue color using Trypan blue dye is loaded into the tip of the straw and the tip of the straw is then heat sealed shut.

The straw is then cooled from approximately room temperature (i.e., about 20° C.) to about −6° C. to −8° C. substantially in a single step, i.e., in less than about 30 seconds of cooling time. At that temperature the straw is seeded by touching the outside surface of the straw with a 1 mm diameter steel rod previously cooled in liquid nitrogen. This induces visible ice formation in compartments 8, 10 and 14 as shown in FIG. 1. The straw is then cooled from the seeding temperature to about −35° C. at a rate of about 0.5° C. per minute, held at about −35° C. for about thirty to sixty minutes and then plunged directly into liquid nitrogen for storage.

When a suitable recipient has been identified and has been determined to be in synchronization with the particular embryo frozen in the straw, the straw is removed from its liquid nitrogen freezing storage container and the solutions contained therein are allowed to rise to ambient temperature which will normally require from about one to two minutes. The user then applies sufficient centrifugal force to the straw either by swinging his arm in an arc or by shaking the straw in the same manner as a thermometer to ensure that the bubbles separating the liquid fractions contained in the straw rise to the top of same, allowing the liquid constituents to mix. Since the straws are clear, visual inspection can ensure that removal of the separating bubbles and contact of the fluids contained in the tube has been accomplished. The straw is then held for a second period of time during which it is preferable to impart a gentle rocking motion to the straw, so as to allow the dilution of the cryoprotective agent described above to occur (usually in the range of from about fifteen to about thirty minutes). The user then cuts off the very bottom of the straw just above the heat seal but within the colored portion of the straw containing the liquid cushioning agent or that portion where the air bubble resides as described in the most preferred embodiment above. The straw is then inserted into an artificial insemination instrument, or gun, and the entire contents of the straw are transferred to the recipient by allowing the plunger of the artificial insemination gun to push the plug at the upper end of the straw through the length thereof delivering the liquid contents and embryo out the open cutoff end of the straw. Transfer to the recipient cow can either be by surgical means (i.e., making an incision along the flank of the animal to expose the uterus and puncturing the uterus to deliver the contents of the straw) or nonsurgically.

Those skilled in the art upon reading the above Detailed Description of the present invention will appreciate that many modifications and alterations of the technique and apparatus described above can be made without departing from the spirit of the invention. All such modifications and alterations which fall within the scope of the appended claims are intended to be covered thereby.

I claim:

1. An apparatus for storing, thawing and transferring frozen embryos to recipients comprising:

(a) a container comprising first and second chambers;

(b) a volume of a cryoprotective solution having said embryo suspended therein contained in said first chamber;

(c) an effective volumetric amount of a diluent solution having a concentration of nontoxic, nonpermeating diluent sufficient to result in a dilution mixture, when combined with said volume of cryoprotective solution, that is substantially isosmolal, contained in said second chamber;

(d) removable separation means dividing said container into said first and second chambers but capable of being removed so as to allow the contents of said first and second chambers to combine and form said dilution mixture.

2. The apparatus of claim 1 wherein said container is tubular.

3. The apparatus of claim 1 wherein said removable separation means comprise air bubbles.

4. The apparatus of claim 2 and further comprising plug means located at the upper end of said tubular container and capable of being pushed through the interior of said tubular container to thereby expel the contents thereof out the other end of said container.

5. The apparatus of claim 1 and further comprising handle means for handling and identifying said frozen embryo without having to touch said container.

6. The apparatus of claim 1 wherein said cryoprotective solution comprises glycerol and said diluent solution comprises sucrose.

7. An apparatus for thawing and transferring a frozen embryo to a recipient animal comprising:

(a) a thin tubular plastic straw of the type typically used in artificial insemination procedures sealed at both ends thereof;

(b) a volume of a cryoprotective agent containing the embryo to be transferred;

(c) an effective volumetric amount for diluting said volume of cryoprotective agent of a diluent solution having a concentration of a nontoxic, nonpermeating compound sufficient to produce a dilution mixture which is substantially isosmolal; and (d) an air bubble separating said volume of cryoprotective agent from said diluent solution.

8. The apparatus of claim 8 and further an effective volumetric amount of a liquid cushioning substance adjacent one end of said straw, said cushioning substance being of sufficient viscosity so as to substantially prohibit said embryo from passing therethrough.

9. The apparatus of claim 8 wherein the front end of said plastic straw is heat sealed and the second end thereof is sealed by a plug of porous material.

10. The apparatus of claim 9 and further comprising a second portion of cryoprotective agent separated from said first portion by a second air bubble and protecting said first portion of cryoprotective agent and embryo from contact with said porous plug.

11. The apparatus of claim 7 and further comprising a handle portion in the form of a straw having an interior diameter slightly greater than the exterior diameter of the straw of said apparatus so that said handle can be slipped over the upper end of said straw and attached for handling and identification purposes.

12. An apparatus for storing, thawing and transferring a frozen embryo to a recipient animal comprising:

(a) a thin tubular plastic straw of the type typically used in artificial insemination procedures comprising a plug of porous material at the first end thereof and the heat seal closure at the second end thereof;

(b) a volume of a cryoprotective agent comprising a solution of glycerol in PBS in a concentration of from about 1.0 M to about 2.0 M said volume containing the embryo to be transferred;

(c) a volumetric amount of a diluent solution from about 6 to about 10 times as great as said volume of cryoprotective agent said diluent solution comprising sucrose in a PBS solution in concentrations of from about 0.5 M to about 1.0 M, the exact concentrations of said cryoprotective agent and diluent solution being adjusted so as to produce a substantially isosmolal condition upon mixture; and (d) an air bubble separating said volume of cryoprotective agent from said diluent solution.

* * * * *

UNITED STATES PATENT AND TRADEMARK OFFICE

CERTIFICATE OF CORRECTION

PATENT NO. : 4,419,986

DATED : December 13, 1983

INVENTOR(S) : Stanley P. Leibo

It is certified that error appears in the above-identified patent and that said Letters Patent is hereby corrected as shown below:

Column 1, line 41, "on" should read -- or --.

Column 4, line 49, "ad" should read -- and --.

Column 4, line 52, after "PBS" delete "] ".

Column 5, line 19, "impossible" should read -- possible --.

Claim 8, line 1, "8" should read -- 7 --.

Claim 8, line 1, after "further" insert -- comprising --.

Claim 9, line 1, "8" should read -- 7 --.

Signed and Sealed this

*Twenty-second* Day of *May 1984*

[SEAL]

*Attest:*

GERALD J. MOSSINGHOFF

*Attesting Officer* *Commissioner of Patents and Trademarks*